United States Patent [19]
Honma et al.

[11] Patent Number: 5,033,293
[45] Date of Patent: Jul. 23, 1991

[54] ALCOHOL CONCENTRATION DETECTING DEVICE

[75] Inventors: Masahiro Honma; Fumio Hagi; Yukihiro Niide; Takenosuke Sano; Koji Iwahashi, all of Tokyo, Japan

[73] Assignee: Calsonic Corporation, Tokyo, Japan

[21] Appl. No.: 491,175

[22] Filed: Mar. 9, 1990

[51] Int. Cl.$^5$ ............................................. G01M 15/00
[52] U.S. Cl. ................................. 73/118.1; 73/61.1 R
[58] Field of Search ........................... 73/118.1, 61.1 R; 324/667, 668, 669; 123/198 D, 198 DC

[56] References Cited

U.S. PATENT DOCUMENTS

| | | | |
|---|---|---|---|
| 3,215,900 | 11/1965 | Harvey | 317/123 |
| 3,368,147 | 2/1968 | Graham | 324/61 |
| 3,778,706 | 12/1973 | Thompson | 324/61 |
| 4,887,023 | 12/1989 | Gimson | 73/61.1 R X |

OTHER PUBLICATIONS

"The Application of Capacitance Type Sensors to the Automobile", Nissan Automotive Technical Report, Dec. 1985, pp. 159-167.

Primary Examiner—Jerry W. Myracle
Attorney, Agent, or Firm—Foley & Lardner

[57] ABSTRACT

An alcohol concentration detecting device is disclosed, which comprises an alcohol sensor of capacitance type having a probe portion which is to be submerged in an alcohol-mixed fuel, the alcohol sensor issuing an output signal which varies in accordance with the concentration of alcohol in the alcohol-mixed fuel; a first oscillating circuit which receives the output signal of the alcohol sensor and issues a variable pulse signal whose duty ratio is variable in accordance with the output signal; a second oscillating circuit which issues a reference pulse signal, the reference pulse signal being the same as the pulse signal which is provided by the first oscillating circuit when there is no alcohol in the fuel; and an alcohol concentration detecting circuit which receives and compares the variable pulse signal and the reference pulse signal and issues an alcohol concentration representing signal which is variable in accordance with a difference in duty ratio between the variable pulse signal and the reference pulse signal.

12 Claims, 10 Drawing Sheets

ALCOHOL CONCENTRATION DETECTING DEVICE

BACKGROUND OF THE INVENTION

1. Field of the Invention

The present invention relates in general to fuel detecting devices which detect a particular component in a mixed fuel, and more particularly to fuel detecting devices of a type which detects the concentration of alcohol (viz., methanol, ethanol or the like) in a mixture of gasoline and alcohol.

2. Description of the Prior Art

For dealing with the energy crisis and air polution problems, it has been proposed to use as the fuel of automotive internal combustion engine a mixed fuel, such as a mixture of gasoline and alcohol.

When such mixed fuel is actually used as the fuel for the engine, it becomes necessary to detect the concentration of alcohol in the mixed fuel in order to appropriately control the substantial air-fuel ratio of the combustible mixture which is fed to the engine.

One of the known devices for detecting the alcohol concentration in the mixed fuel is disclosed in NISSAN AUTOMOTIVE TECHNICAL REPORT (issued from NISSAN MOTOR CO., LTD. in December, 1985). In this device, a so-called "capacitance type alcohol sensor" is used, which comprises a pair of spaced electrode plates which are to be submerged in the mixed fuel. In operation, the capacitance established between the two electrode plates in the fuel is measured to obtain the dielectric constant of the fuel, and the alcohol concentration is derived from the dielectric constant.

In order to clarify the aim of the present invention, the conventional device disclosed by the REPORT will be outlined in the following with reference to FIG. 15 of the accompanying drawings.

Figures 13, 15:
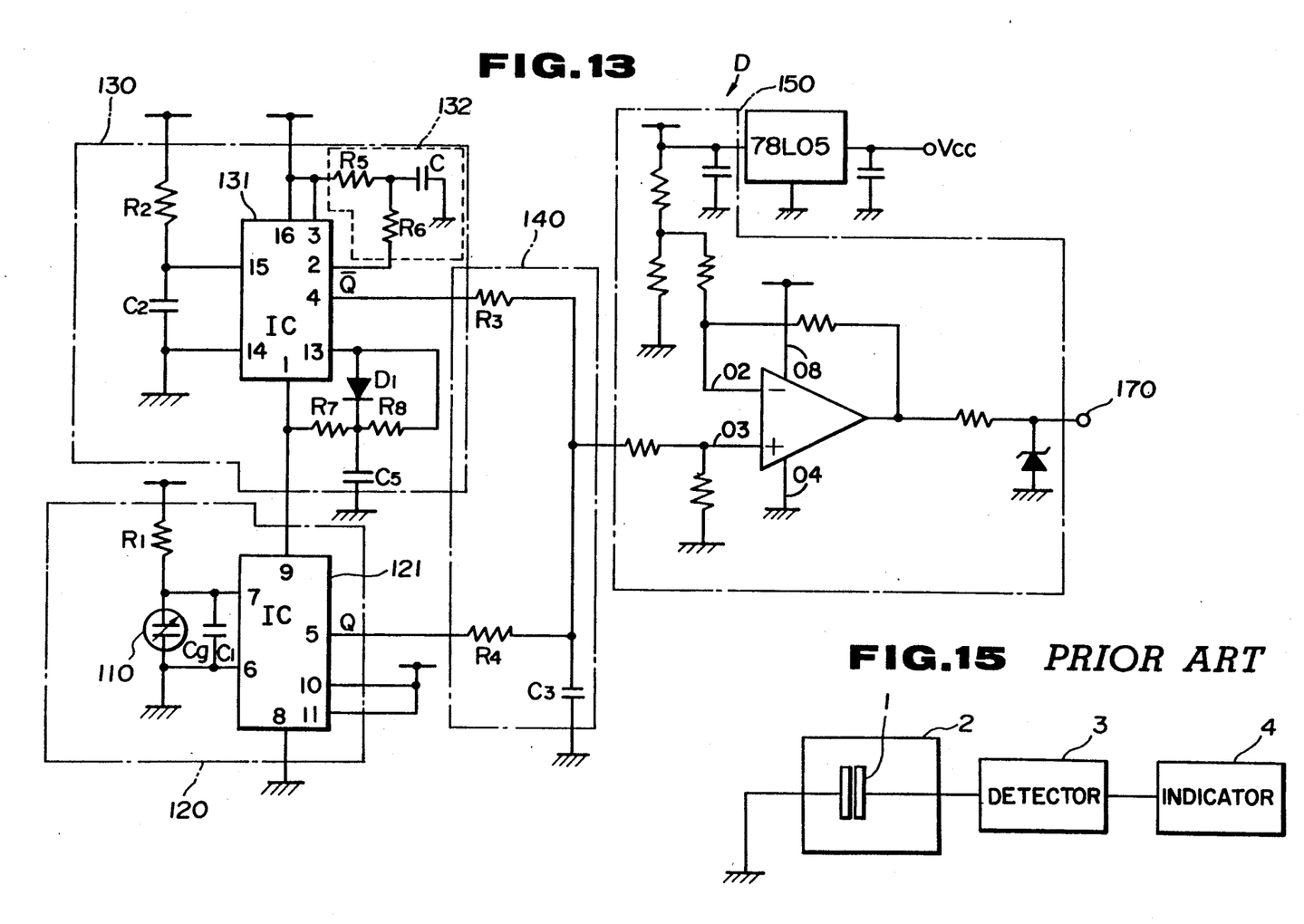
FIG. 13 is a circuit diagram of an alcohol concentration detecting device which is a fourth embodiment of the present invention.
FIG. 15 is a block diagram of one conventional alcohol concentration detecting device.

As is seen from FIG. 15, the device comprises the capacitance type alcohol sensor 1 which has a pair of spaced electrode plates submerged in alcohol-mixed fuel in a fuel tank 2. The change in the capacitance established between the two electrode plates is processed by a detecting circuit 3 in which the capacitance change is converted into a current change or signal frequency change for calculating the alcohol concentration in the mixed fuel. The detecting circuit 3 includes a correction unit by which the current change or signal frequency change is corrected in accordance with the temperature of the mixed fuel. An indicating device 4 receives the corrected signal (viz., current change or signal frequency change) from the detecting circuit 3 and processes the signal to give a visual indication of the alcohol concentration.

However, due to its inherent construction, the above-mentioned device has the following drawbacks.

First, since the capacitance sensed by the alcohol sensor is directly fed to the detecting circuit 3, it is very difficult to pick up, from the sensed capacitance information, only the component which represents the alcohol concentration.

Furthermore, in the measuring method employed in the device, it is very difficult to reduce or minimize unavoidable errors in the signal from the detecting circuit 3, the errors being particularly caused by the ambient temperature (that is, the engine room temperature in which the detecting circuit is installed). This means that the device is not suitable for a motor vehicle which is subjected to a wide ranging movement from a cold area to a hot area and vice versa.

SUMMARY OF THE INVENTION

It is therefore an object of the present invention to provide an alcohol concentration detecting device which is free of the above-mentioned drawbacks.

According to the present invention, there is provided an alcohol concentration detecting device which comprises an alcohol sensor of the capacitance type having a probe portion which is to be submerged in an alcohol-mixed fuel, the alcohol sensor outputting an output signal which varies in accordance with the concentration of alcohol in the alcohol-mixed fuel; a first ocsillating circuit which receives the output signal of the alcohol sensor and outputs a variable pulse signal whose duty ratio is variable in accordance with the output signal; a second oscillating circuit which outputs a reference pulse signal, the reference pulse signal being the same as the pulse signal which is provided by the first oscillating circuit when there is no alcohol in the fuel; and an alcohol concentration detecting circuit which receives and compares the variable pulse signal and the reference pulse signal and outputs an alcohol concentration representing signal which is variable in accordance with a difference in duty ratio between the variable pulse signal and the reference pulse signal.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

In the following, five embodiments of the present invention will be described with reference to the accompanying drawings.

Referring to FIGS. 1 to 5 of the drawings, there is shown an alcohol concentration detecting device "A" which is a first embodiment of the present invention. As is understood from FIG. 4, the device "A" is designed to detect the concentration of alcohol in an alcohol-mixed gasoline in an automotive fuel tank 100.

Figure 1:
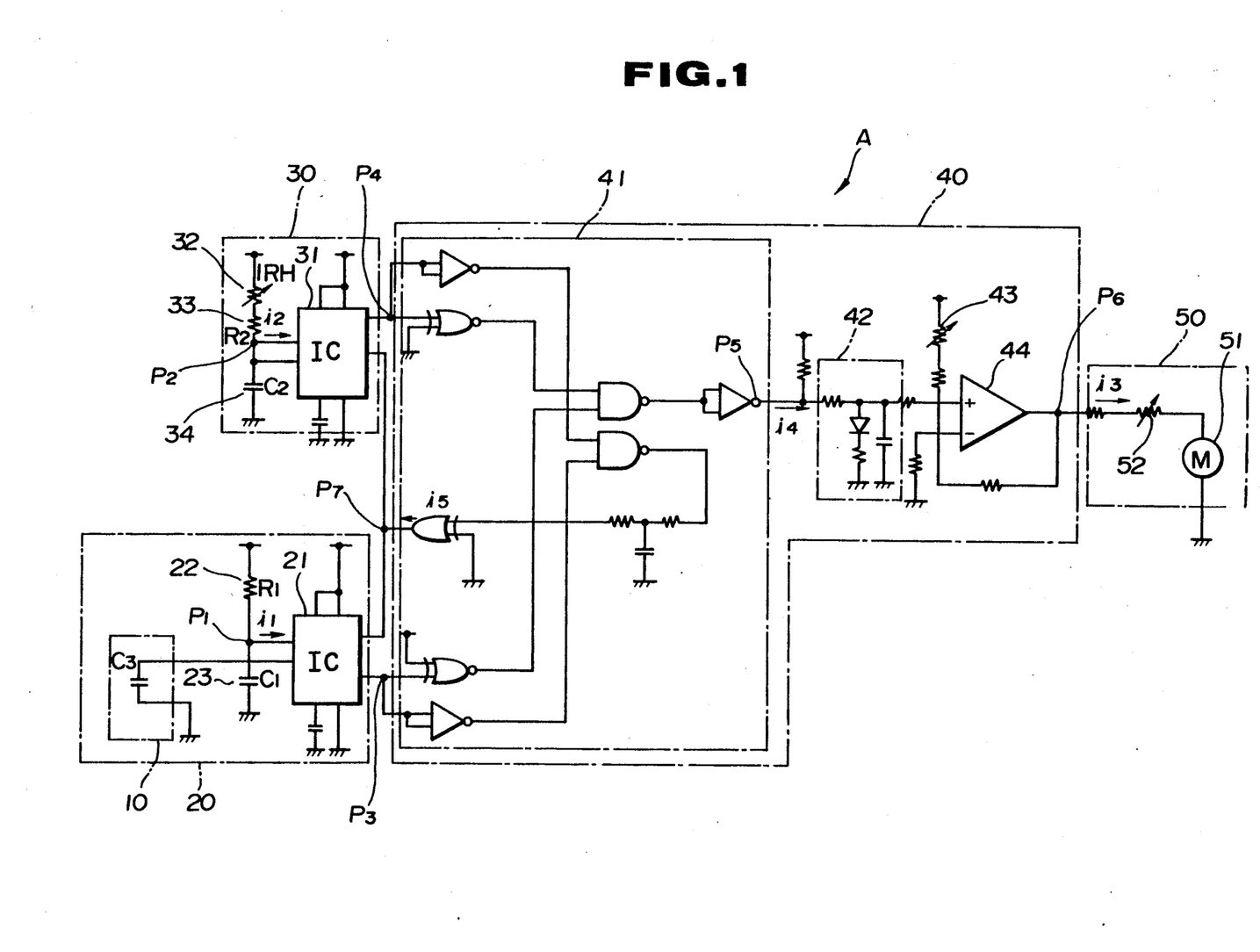
FIG. 1 is a circuit diagram of an alcohol concentration detecting device which is a first embodiment of the present invention.

As is seen from FIG. 1, the device "A" comprises generally an alcohol sensor 10, a first oscillating circuit 20, a second oscillating circuit 30, an alcohol concentration detecting circuit 40, and an indicating circuit 50.

The alcohol sensor 10 is of the above-mentioned capacitance type, which senses the capacitance "Cg" due to the mixed fuel in the fuel tank. As is seen from FIG. 3, the alcohol sensor 10 comprises an inner cylindrical electrode 11 and an outer cylindrical electrode 12 which are arranged coaxially. The outer cylindrical electrode 12 has an axially extending slit 13. The slit 13 permits smooth flowing of the fuel into a cylindrical clearance defined between the inner and outer cylindrical electrodes 11 and 12.

Figures 2, 3:
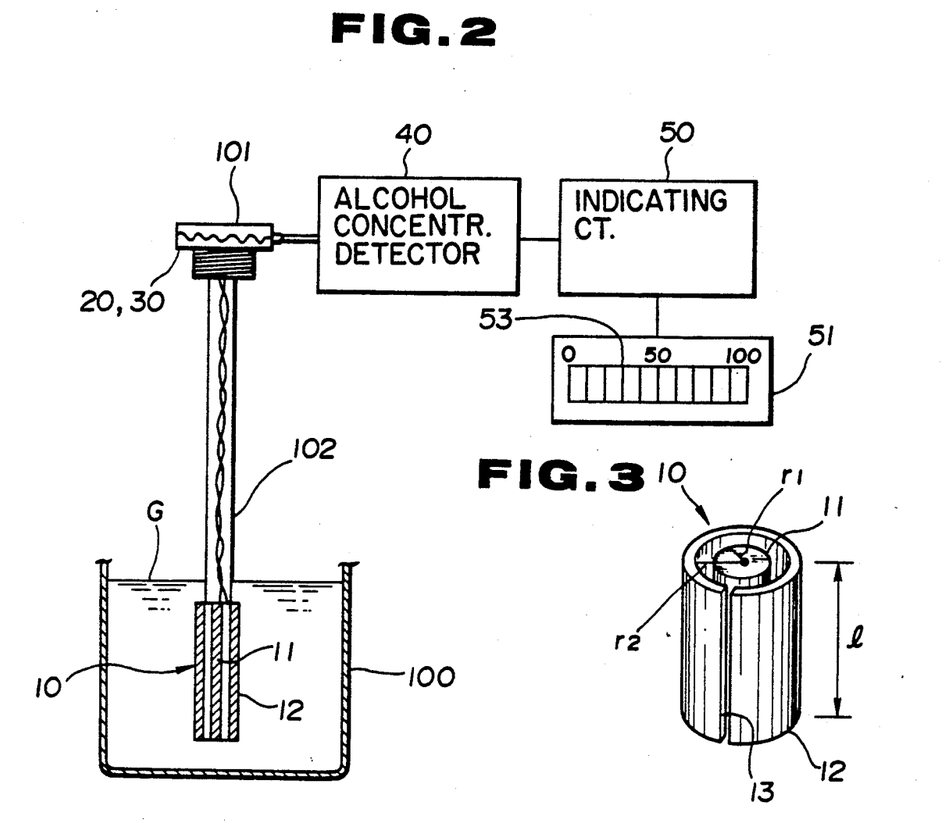
FIG. 2 is a block diagram of the first embodiment.
FIG. 3 is a perspective view of an alcohol sensor employed in the first embodiment.

When the sensor 10 is submerged in the alcohol-mixed fuel, the capacitance "Cg" established between the two electrodes 11 and 12 is expressed by the following equation.

$$Cg = 2\pi\epsilon \cdot l / \ln(r2/r1) \ldots \quad (1)$$

wherein
- $\epsilon$: dielectric constant of a mixed fuel,
- l: length of each electrode 11 or 12,
- r1: outer diameter of internal electrode 11,
- r2: inner diameter of outer electrode 12.

At 20° C., the dielectric constant of gasoline, ethanol and methanol are about 2.0, 25.1 and 33.6 respectively. Thus, when gasoline is mixed with one of the alcohols at a certain mixing ratio, the dielectric constant of the mixed fuel changes in accordance with the mixing ratio. Thus, the mixing ratio of the alcohol in the fuel (viz., the alcohol concentration) can be measured by detecting the capacitance "Cg".

As is seen from FIG. 2, in practice, the alcohol sensor 10 is installed in a lower part of a tubular holder 102. The tubular holder 102 has at its upper end a threaded lid 101 secured thereto. Upon assembly, the threaded lid 101 is screwed into a threaded bore formed in an upper part of the fuel tank 100 with the tubular holder 102 projected into the fuel tank 100. Known lead wires from the electrodes 11 and 12 extend in and through the tubular holder 102 toward the lid 101. Preferably, the tubular holder 102 is made flexible. For this, the holder 102 may be constructed of a flexible plastic tube, a flexible tube consisting of a coiled wire, or the like.

The lid 101 holds therein a base plate on which the first oscillating circuit 20, the second oscillating circuit 30 and the alcohol concentration detecting circuit 40 are compactly installed.

The first oscillating circuit 20 is for generating a pulse signal of a frequency "f1" which is variable in accordance with the capacitance sensed by the alcohol sensor 10. The first oscillating circuit 20 includes a fixed resistor 22, a condenser 23 and an integrated circuit 21 which are connected as is shown in FIG. 1.

The first oscillating circuit 20 charges the condenser 23 at a time constant represented by:

$$\tau 1 = R1 \cdot (C1 + Cg) \ldots \quad (2)$$

wherein:
- $\rho 1$: time constant,
- R1: resistance of resistor 22,
- C1: capacitance of condenser 23.

When a voltage appearing at the condenser 23 reaches a threshold level, an electric discharge occurs. From this, as is seen from the uppermost part (1) of the time chart in FIG. 5, a pulse signal "i1" is produced, which appears at the point "P1" of the circuit of FIG. 1. In part (1), the pulse signal illustrated by a solid line is the signal produced when no alcohol is contained in the fuel, while the pulse signal illustrated by a broken line is the signal produced when alcohol is contained in the fuel.

Figure 5:
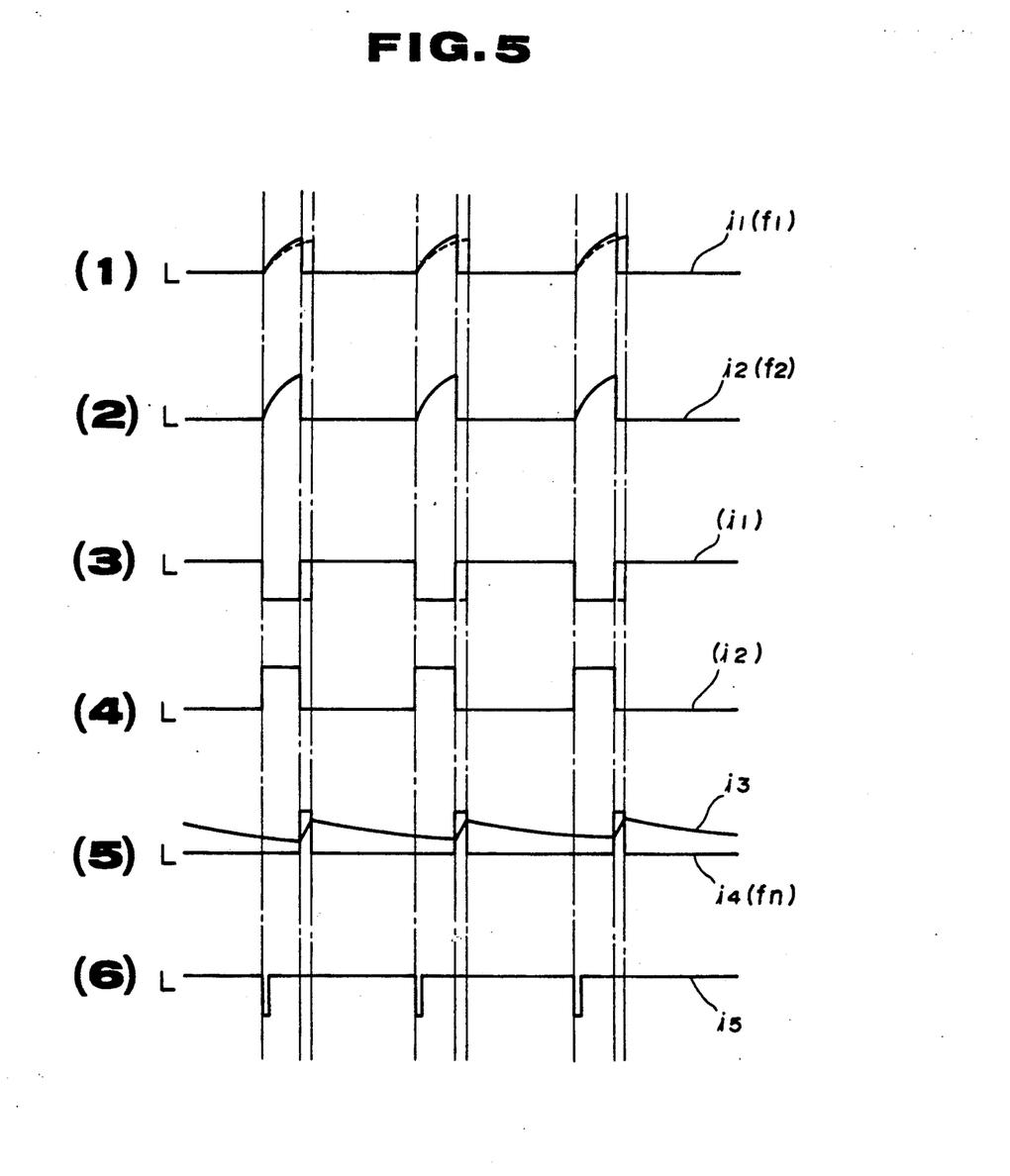
FIG. 5 is a time chart showing wave forms of various pulse signals produced in various circuits employed in the first embodiment.

The second oscillating circuit 30 is for generating a reference pulse signal of a frequency "f2" as is illustrated in part (2) of the time chart of FIG. 5. The frequency "f2" is the same as the aforementioned frequency "f1" of the signal "i1" which is produced at the time when the fuel has no alcohol contained therein.

The second oscillating circuit 30 includes a first variable resistor 32, a fixed resistor 33, a condenser 34 and an integrated circuit 31 which are connected as is shown in FIG. 1.

The second oscillating circuit 30 charges the condenser 34 with a time constant represented by:

$$\tau 2 = (1RH + R2) \cdot C2 \ldots \quad (3)$$

wherein:
- $\tau 2$: time constant,
- 1RH: resistance of variable resistor 32,
- R2: resistance of resistor 33,
- C2: capacitance of condenser 34.

When a voltage appearing at the condender 34 reaches to a threshold level, an electric discharge occurs. With this, as is seen from part (2) of the time chart in FIG. 5, the pulse signal "i2" is produced, which appears at the point "P2" of FIG. 1.

It is to be noted that the condensers 23 and 34 satisfy the following equation:

$$C2 = C1 + Cg_0 \ldots \quad (4)$$

wherein
- $Cg_0$: capacitance sensed by sensor 10 when no alcohol is contained in fuel.

The alcohol concentration detecting circuit 40 is a circuit for producing an alcohol concentration signal "i3" by processing the above-mentioned two pulse signals "i1" and "i2". That is, in the circuit 40, the duty ratios of the respective pulse signals "i1" and "i2" are compared to provide a duty ratio difference therebetween, and the alcohol concentration signal "i3" is produced in accordance with the duty ratio difference.

As is seen from FIG. 1, the alcohol concentration detecting circuit 40 comprises a so-called shaping and comparing circuit 41, a F/V conversion circuit 42 and an amplifying circuit 44.

In the shaping and comparing circuit 41, the waveforms of the pulse signals "i1" and "i2" are shaped to be rectangular pulse signals. The rectangular waveforms thus shaped are respectively shown in parts (3) and (4) of the time chart of FIG. 5, which appear at the points "P3" and "P4" of the circuit of FIG. 1.

That is, the signal shown by the part, (1) is fed to the IC-21 and wave-shaped to have an inverted rectangular waveform as shown in part (3). The signal shown by part (2) is fed to the IC-31 and wave-shaped to have a rectangular waveform as shown in part (4).

After completion of the waveform shaping, the circuit 41 compares these two shaped pulse signals to produce a duty ratio difference signal "i4" which is illustrated in part (5) of the time chart of FIG. 5 and appears at the point "P5" of the circuit. It is to be noted that the signal "i3" which appears at the point "P6" of the circuit, is produced by smoothing the signal "i4".

It is to be noted that the pulse signal "i5" shown in part (6) of the time chart is a reset signal for resetting operation of the IC-31 and IC-21.

The F/V conversion circuit 42 and the amplifying circuit 44 function to smooth the duty ratio difference signal "i4" and amplify the smoothed signal to provide the afore-mentioned alcohol concentration signal "i3" which is to be fed to the indicating circuit 50.

It is to be noted that a second variable resistor 43 arranged in the alcohol concentration detecting circuit 40 is used for zero-adjusting a meter 51 of the indicating circuit 50.

The indicating circuit 50 comprises the indicating meter 51 which is arranged on an instrument panel of the motor vehicle. The meter 51 has a pointer which is movable to point to a corresponding graduation of alcohol concentration on a calibrated board in accordance with the alcohol concentration signal "i3". Preferably, the meter 51 is designed to indicate alcohol concentration from 0% to 100%. A third variable resistor 52 employed in the indicating circuit 50 is used for adjusting the gain of the meter 51. Of course, a digital type indicating meter is also employable.

In order to adjust the alcohol concentration detecting device "A", the following steps are taken.

First, the first variable resistor 32 is manipulated to equalize the frequencies "f1" and "f2" of the two pulse signals "i1" and "i2" for obtaining the condition wherein the duty ratio difference therebetween is zero, and the second variable resistor 43 is manipulated to cause the pointer 53 of the meter 51 to point to the "zero" mark.

Then, the alcohol sensor 10 is put into a standard mixed fuel which contains 50 wt % alcohol and 50 wt % gasoline, and the third variable resistor 52 is manipulated to permit the pointer 53 of the meter 51 to point to the 50% mark.

In the following, operation of the alcohol concentration detecting device "A" will be described with reference to the drawings.

Figure 4:
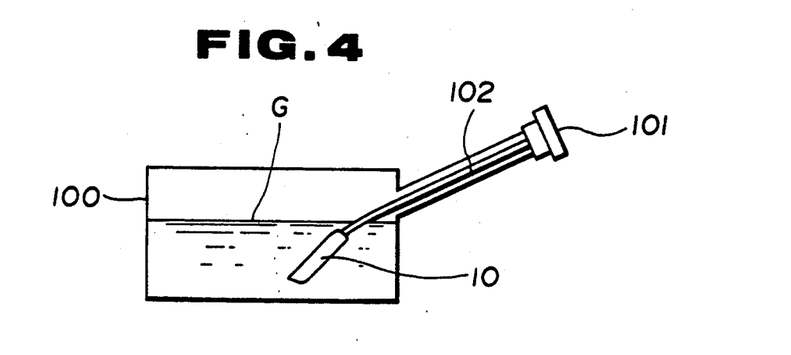
FIG. 4 is a sectional view showing a fuel tank into which the alcohol concentration detecting device of the first embodiment is installed in practice.

A description will be provided with respect to a condition wherein the alcohol sensor 10 has been already submerged in the fuel tank 100 as shown in FIGS. 2 and 4.

When some alcohol is contained in the fuel in the fuel tank 100, the alcohol sensor 10 senses the capacitance "Cg", and thus, the duty ratio difference signal "i4" as shown in part (5) of FIG. 5 is produced. The signal "i4" is processed by the F/V conversion circuit 42 to produce the alcohol concentration signal "i3". With this, the pointer 53 of the meter 51 is moved to point at a certain % mark on the calibrated board.

In the following, the advantages of the first embodiment of the present invention will be described.

First, due to provision of the first oscillating circuit 20, the very small change of the capacitance sensed by the alcohol sensor 10 can be converted into a considerably large change in the frequency of the pulse signal "i1". Thus, the undesired effect caused by noise is reduced and thus, very precise alcohol concentration detection is achieved. Due to the same reason, the alcohol concentration detecting device can be made compact in size.

Second, at the alcohol concentration detecting circuit 40, a comparison is carried out between the variable pulse signal "i1" and the reference pulse signal "i2" to pick up, from the variable pulse signal "i1", only the comPonent representative of the alcohol concentration in the fuel. Thus, alcohol concentration detection is precisely and easily achieved.

Third, the first and second oscillating circuits 20 and 30 are, both installed in the same lid 101. Thus, the same temperature is applied to these two circuits 20 and 30. This induces a mutual cancellation of any temperature disturbance having substantially no effect on the alcohol concentration detection carried out by the detecting device "A". Furthermore, since the first oscillating circuit 20 is installed in the lid 101 which is placed very near the alcohol sensor 10, the electric wires extending therebetween can be reduced in length. This suppresses or at least minimizes noise which is deleteriously applied to the device "A". That is, the S/N ratio of the signal transmitted through the electric wires is increased. Furthermore, any undesired stray capacitance between the electric wires is reduced.

Referring to FIGS. 6 to 9, there is shown an alcohol concentration detecting device "B" of a second embodiment of the present invention. The device "B" of this second embodiment is somewhat improved as compared with the afore-mentioned first embodiment. That is, as will be understood from the following description, in this second embodiment, a measure is used for improving the starting operation of the oscillating circuits employed in the device.

Figure 6:
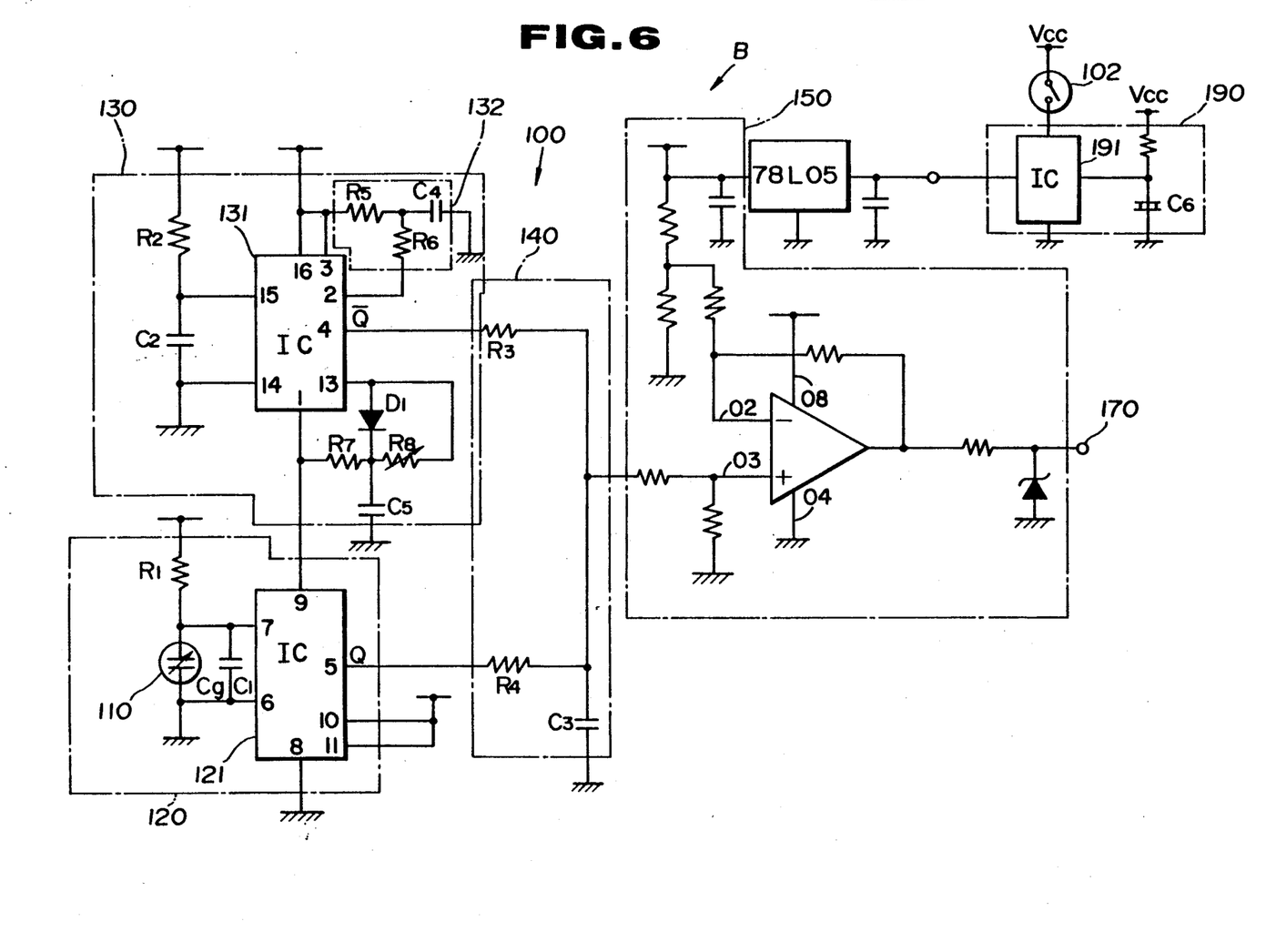
FIG. 6 is a circuit diagram of an alcohol concentration detecting device which is a second embodiment of the present invention.

As is seen from FIG. 6, the alcohol concentration detecting device "B" comprises an alcohol sensor 110, a first oscillating circuit 120, a second oscillating circuit 130, a F/V conversion circuit 140, an amplifying circuit 150 and a timer circuit 190.

Figure 7:
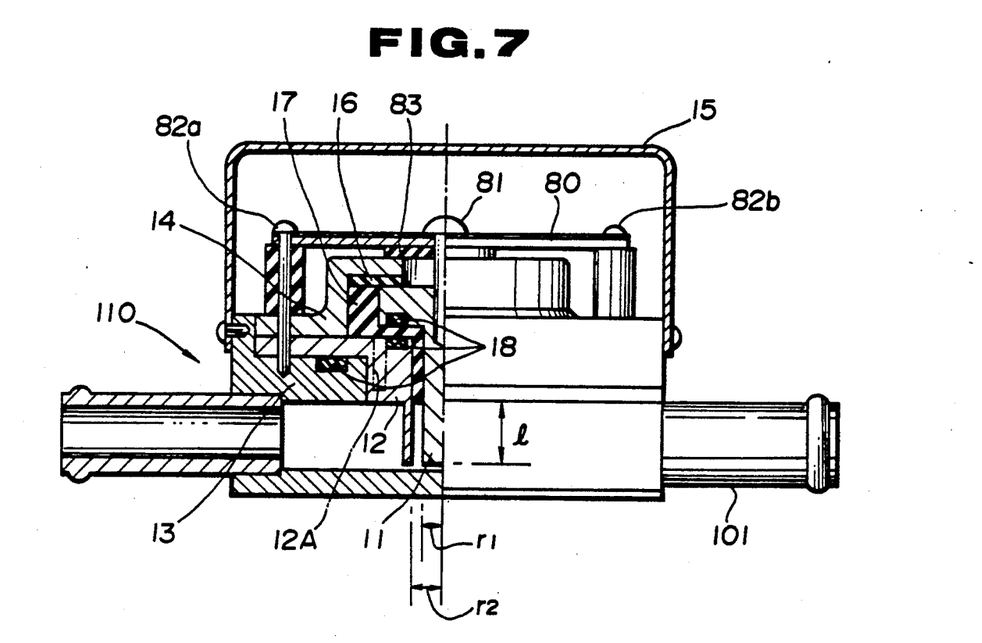
FIG. 7 is a half sectional view of an alcohol sensor employed in the second embodiment.

The alcohol sensor 110 is of the above-mentioned capacitance type, which comprises, as is seen from FIG. 7, an inner cylindrical electrode 11 and an outer cylindrical electrode 12 which are arranged coaxially. Unlike the case of the first embodiment, in the second embodiment, the alcohol sensor 110 is installed in a fuel pipe 101 which extends from a fuel tank (not shown) to an engine (not shown).

The detailed construction of such alcohol sensor 110 is shown in U.S. Patent Application No. 07/379,883 filed on July 14, 1989 in the name of NOGAMI and NUNOKAWA now U.S. Pat. No. 4,939,467. That is, the alcohol sensor comprises a lower case 13, an upper case 14, a metal cover 15, insulators 16 and 17, and seals 18.

Within the cover 15, there is arranged a base board 80 which is mounted on the alcohol sensor 110 by means of electrically conducting connecting bolts 81, 82a and 82b. The first oscillating circuit 120, the second oscillating circuit 130, the F/V conversion circuit 140, the amplifying circuit 150 and the timer circuit 190 are all mounted on the same base board 80 to constitute a detecting circuit 100. Between, the base board 80 and the upper case 14, there is placed an insulating member 83.

Referring back to FIG. 6, the first oscillating circuit 120 is for generating a pulse signal of a frequency "f1" in accordance with the capacitance "Cg" sensed by the alcohol sensor 110. The first oscillating circuit 120 comprises a fixed resistor (R1), a condenser (whose capacity is C1) and an integrated circuit 121 which are connected in the illustrated manner. It is to be noted that numerals enclosed by respective circles at the integrated circuit 121 denote respective terminals provided for the circuit 121.

Figure 8:
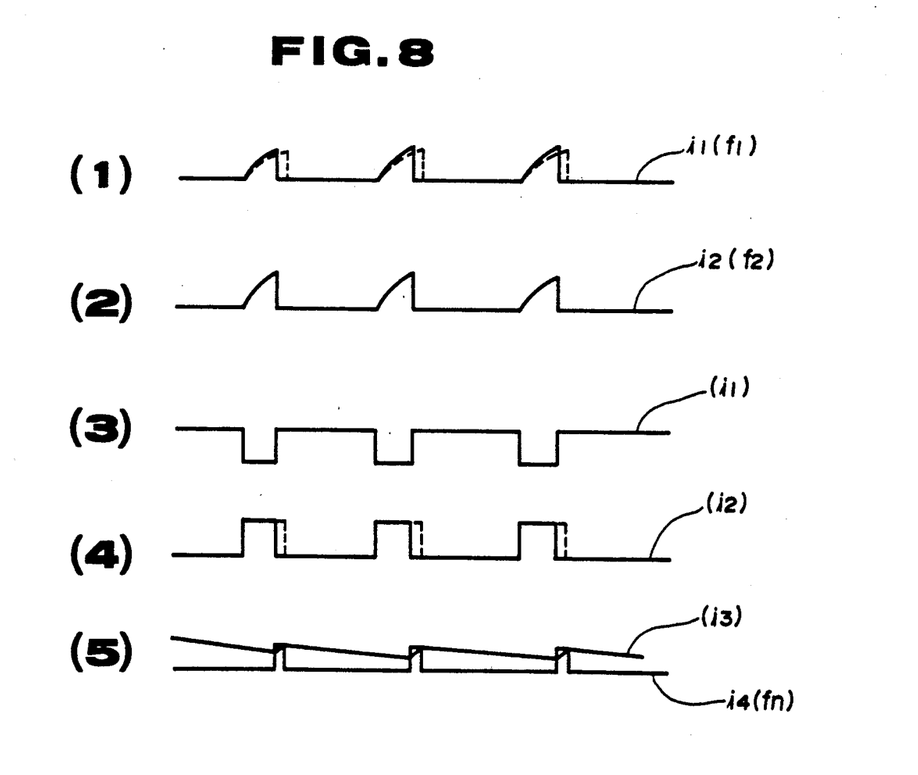
FIG. 8 is a time chart showing waveforms of various pulse signals produced in various circuits employed in the second embodiment.

The first oscillating circuit 120 charges the condenser "C1" at a time constant determined by the integrated circuit 121. When a voltage appearing at the condenser "C1" reaches a threshold level, an electric discharge occurs, so that such a variable pulse signal "i1" as shown in uppermost part (1) of FIG. 8 is produced. In part (1), the pulse signal illustrated by a solid line is the signal produced when no alcohol is contained in the fuel, while the pulse signal illustrated by a broken line is the signal produced when alcohol is contained in the fuel.

The second oscillating circuit 130 is for generating a pulse signal of a frequency "f2". It is to be noted that the frequency "f2" is the same as the frequency "f1" of the signal which is produced at the time when no alcohol is contained in the fuel. The second oscillating circuit 130 charges condenser C2 (whose capacity is C2) at a time constant determined by an integrated circuit 131. When a voltage appearing at the condenser "C2" reaches a threshold level, an electric discharge occurs to produce a signal pulse "i2" as shown in part (2) of FIG. 8.

It is to be noted that in the second embodiment, the following equation is established.

$$C2 \leq C1 + Cg \ldots (5)$$

As shown in FIG. 6, the integrated circuit 131 has second, third and sixteenth terminals connected to a delay circuit 132.

The delay circuit 132 comprises two fixed resistors (R5, R6) and a condenser (C4). With this delay circuit 132, the application of a voltage to these three terminals is somewhat delayed as compared with the remaining terminals.

Experiment has revealed that due to the presence of the delay circuit 132, the second oscillating circuit 130 can issue a very stable reference pulse signal.

The F/V conversion circuit 140 is for producing an alcohol concentration signal "i3" by processing the above-mentioned two pulse signals "i1" and "i2". That is, in the circuit 140, the duty ratios of the two pulse signals "i1" and "i2" are compared to determine a duty ratio difference therebetween, and the alcohol concentration signal "i3" is produced in accordance with the duty ratio difference. As is shown in FIG. 6, the F/V conversion circuit 140 comprises fixed resistors (R3, R4) and a condenser (C3).

That is, in the F/V conversion circuit 140, the waveforms of the pulse signals "i1" and "i2" are shaped in accordance with their frequencies "f1" and "f2" to output rectangular pulse signals as shown in parts (3) and (4) of the time chart of FIG. 8. After completion of this waveform shaping, these rectangular pulse signals are compared to produce a duty ratio difference signal "i4" which is illustrated in part (5) of the time chart of FIG. 8. The duty ratio difference signal "i4" is then fed to the amplifying circuit 150 to produce the alcohol concentration signal "i3" as shown in part (5) of the time chart of FIG. 8.

The alcohol concentration signal "i3" may be fed through an output terminal means 170 to a known controller (not shown) which controls the air-fuel ratio, the ignition timing and the like of the associated engine.

Figure 9:
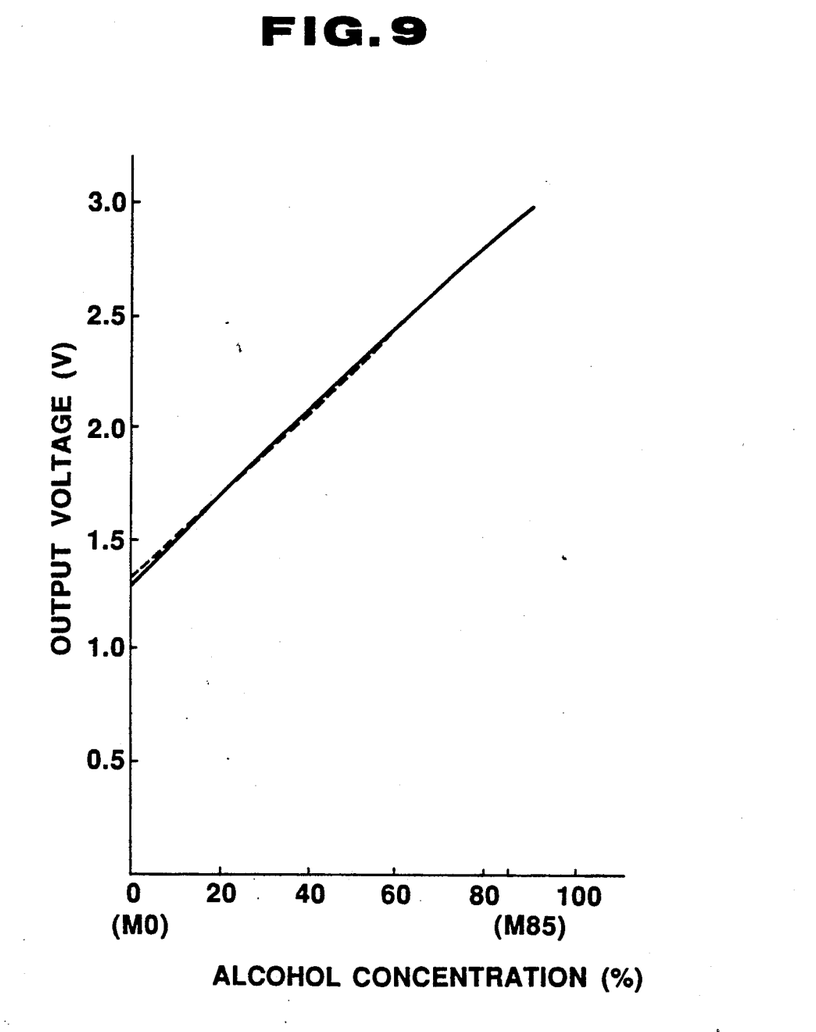
FIG. 9 is a graph showing the characteristic of the second embodiment in terms of the relationship between an output voltage and alcohol concentration.

FIG. 9 is a graph showing the relationship between the voltage of the alcohol concentration signal "i3" and the alcohol concentration in an alcohol mixed fuel. The solid line shows the relationship when the temperature of the fuel 25° C., and the broken line shows the relationship when the temperature of the fuel is 85° C.

Referring back to FIG. 6, the detecting circuit 100 is connected through the timer circuit 190 to an ignition switch 102 of the engine. The timer circuit 190 has an integrated circuit 191 arranged therein.

When the ignition switch 102 is ON, the timer circuit 190 starts and permits operation of the detecting circuit 100 for a given time. After the given time, the timer circuit 190 stops the operation of the detecting circuit 100. This means that the time during which a certain voltage is applied between the two electrodes 11 and 12 of the alcohol sensor 110 is only the given time. Thus, the electric erosion of the positive electrode 11 and the attachment of ionized metals to the negative electrode 12 are considerably reduced. In other words, alcohol concentration detection is carried out for only a given time each time the ignition switch is turned ON.

In the following, advantages of the second embodiment of the present invention will be described.

First, due to the provision of the delay circuit 132, the accuracy of the second oscillating circuit 132 is improved. Thus, more precise alcohol concentration detection is carried out by device "B".

Second, due to the provision of the timer circuit 190, the undesired electric erosion of the positive electrode 11 and the attachment of ionized metals to the negative electrode 12 are reduced.

Third, since the first oscillating circuit 120 is installed in the metal cover 15 of the alcohol sensor 110 near the electrodes 11 and 12, the electrically conducting members extending therebetween can be reduced in length. This arrangement thus suppresses or at least minimizes noise which would be applied to device "B".

Figure 10:
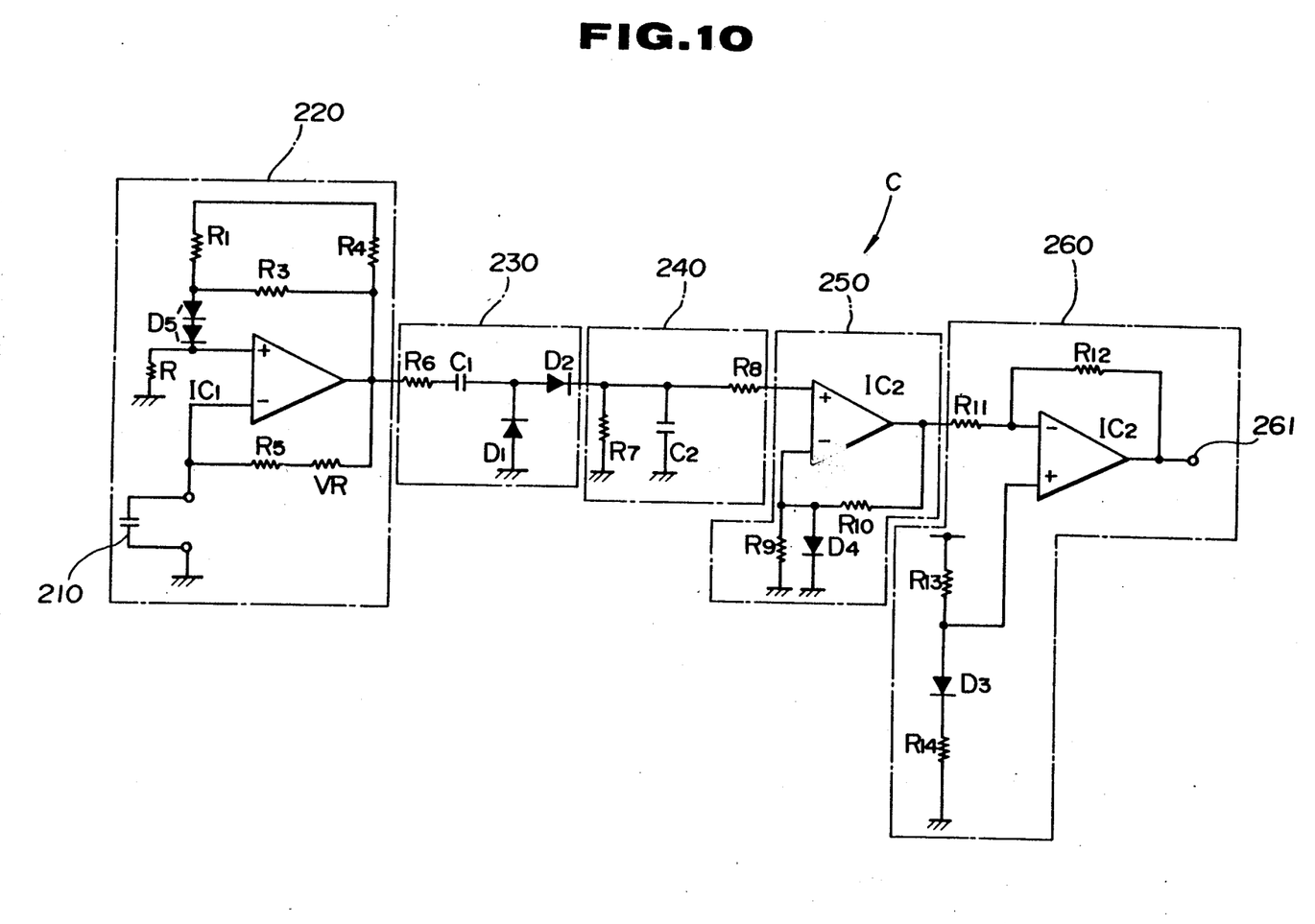
FIG. 10 is a circuit diagram of an alcohol concentration detecting device which is a third embodiment of the present invention.
Figure 11:
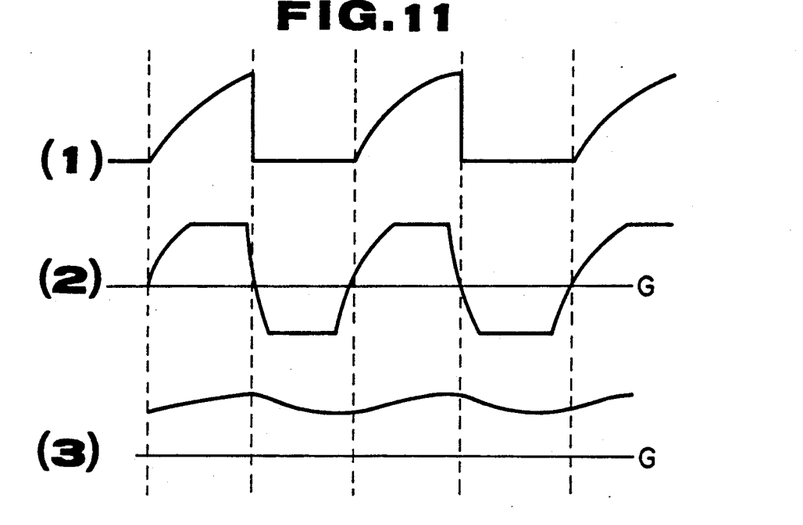
FIG. 11 is a time chart showing waveforms of various pulse signals produced in various circuits employed in the third embodiment.
Figure 12:
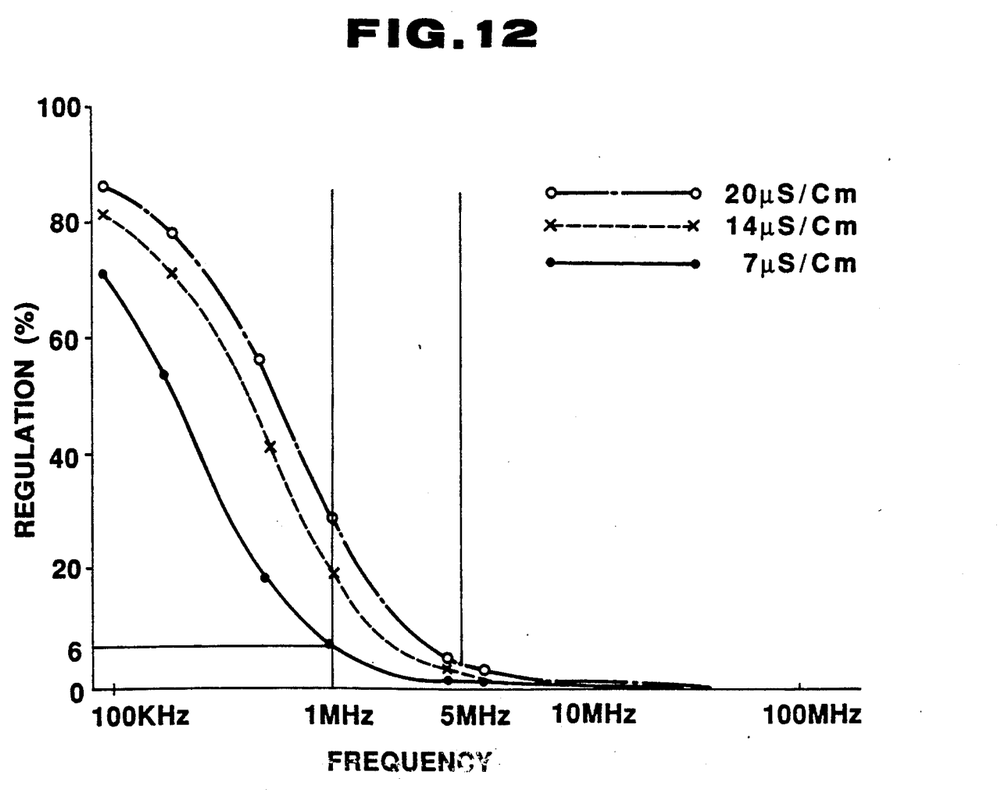
FIG. 12 is a graph showing the characteristics of three types of methanol-mixed fuel in terms of the relationship between the frequency of a pulse produced by the oscillating circuit and the regulation of the impedance appearing between positive and negative terminals of an alcohol sensor.

Referring to FIGS. 10 to 12, there is shown an alcohol concentration detecting device "C" of a third embodiment of the present invention. As will become apparent as the description proceeds, the device "C" of the third embodiment is designed to exhibit superior detecting performance without being affected by ionized metals in the alcohol mixed fuel.

As is seen from FIG. 10, the alcohol concentration detecting device "C" comprises an alcohol sensor 210, an oscillating circuit 220, a differentiating circuit 230, an integrating circuit 240, an amplifying circuit 250 and a signal inverting circuit 260.

The alcohol sensor 210 is of the capacitance type, which is the same as the alcohol sensor 110 (see FIG. 7) employed in the above-mentioned second embodiment "B".

In order to minimize the influence of ionized metals in the fuel, the alcohol sensor 210 is designed to have a very small capacitance "Cg" of about 2 pF to 10 pF when submerged in gasoline.

Similar to the case of the second embodiment "B", the circuits 220, 230, 240, 250 and 260 are all installed on the base board 80 of the alcohol sensor 210.

The oscillating circuit 220 is for generating a pulse signal of a frequency of about 2 MHz to 5 MHz in accordance with the capacitance sensed by the alcohol sensor 210. The waveform of the pulse signal produced by the oscillating circuit 220 is shown in the uppermost part (1) of the time chart of FIG. 11.

The signal is fed to the differentiating circuit 230 where wave shaping is carried out to produce a signal as shown in part (2) of FIG. 11. The signal is then fed to the integrating circuit 240 where further wave shaping is carried out to produce a signal as shown in part (3) of FIG. 11. The signal is then fed to the inverting circuit 260 and a voltage is output from an output terminal 261 of the circuit 260.

The voltage output is fed to a known controller (not shown) to control the operation of the engine.

It is to be noted that the diodes "D3, D4 and D5" in the circuits 220, 250 and 260 are used for achieving temperature compensation.

FIG. 12 is a graph showing the characteristics of three types of methanol-mixed fuel in terms of the relationship between the frequency of a pulse produced by the oscillating circuit and the regulation of the impedance appearing between the positive and negative terminals of the alcohol sensor. The electric conductivities of these three types are 7, 14 and 20 μs/cm, respectively.

As is seen from this graph, when the frequency of the oscillating pulse is too low, the regulation of the impedance is increased. This means that when the frequency of the oscillating pulse is too low, the influence of foreign components (viz., ionized metals, water and the like) in the fuel on the output of the alcohol sensor appreciable. In fact, the electric conductivity of fuel increases with an increase of foreign components in the fuel.

While, when the frequency of the oscillating pulse is too high, it becomes necessary to force the sensor to have a reduced detecting capacity due to the inherent construction of the signal processing circuit of the sensor. However, in this case, the output of the sensor is greatly affected by the stray capacity of the sensor, and furthermore, the circuit for producing the high frequency oscillator pulse is complicated, resulting in greater cost.

For the reasons mentioned hereinabove, in accordance with the present invention, the frequency of the oscillator pulse is determined to be within a range from 1 to 5 MHz.

It is known that when some foreign components are added to a gasoline-alcohol mixed fuel, the electric conductivity of the fuel shows about 7 μs/cm as the maximum. Thus, when, as is seen from the graph, the frequency is set within the above-mentioned predetermined range, it is possible, to reduce the regulation of the impedance to be lower than 6% and thus the detecting accuracy of the alcohol concentration detecting device is greatly improved.

In the following, advantages of the third embodiment "C" will be described.

First, since the alcohol sensor 210 is constructed to have a very small capacitance "Cg" of about 2 pF to 10 pF when the same is submerged in the alcohol mixed fuel, the influence of ionized metals in the fuel on the detecting accuracy of the device "C" is minimized.

Second, since the frequency of the pulse signal provided by the oscillating circuit 220 is controlled to be within the range from 1 MHz to 5 MHz, not only a stable dielectric constant but also a reduced loss angle is obtained. Thus, the alcohol concentration, detecting ability of the device "C" is improved.

Referring to FIG. 13, there is shown an alcohol concentration detecting device "D" of a fourth embodiment of the present invention.

Since the fourth embodiment "D" is similar to the afore-described second embodiment "B", only the parts different from those of the second embodiment "B" will be described in the following.

As is seen from FIG. 13, in the device "D" of this fourth embodiment, there is no circuit which corresponds to the timer circuit 190 employed in the second embodiment "B".

In the fourth embodiment "D", the capacity of the condenser "C1", in the first oscillating circuit 120 is determined to be somewhat higher than the internal capacity of the integrated circuit 121. That is, if the internal capacity (viz., stray capacity) of the integrated circuit 121 is about 50 pF, the capacity of the condenser "C1" is determined about 75 pF.

In the fourth embodiment "D", the alcohol sensor 110 has a very small internal capacitance of about 2 pF.

Furthermore, in the fourth embodiment, the capacity of the condenser "C2" of the second oscillating circuit 130 is determined to be higher than the stray capacity of the integrated circuit 131.

In the following, an important advantage of the fourth embodiment "D" will be described.

That is, the condenser "C1" in the first oscillating circuit 120, has a capacity which is higher than the internal capacity of the integrated circuit 121. This means that various components of the internal capacity, which are subjected to change upon temperature change, are cancelled. Thus, a very small change of the capacitance sensed by the alcohol sensor 110 can be precisely measured.

That is, if the internal capacity of the integrated circuit 121 is affected by temperature, the circuit 121 tends to change the duty value and wavelength of the pulse signal issued therefrom. However, provision of the condenser "C1" eliminates this drawback. More specifically, although the provision of the first and second oscillating circuits 120 and 130 on the same base board 80 brings about the mutual cancellation of the temperature disturbance applied to the pulse signals "i1" and "i2", the change in the frequency of the signals from the circuits causes a change in the capacitance-frequency characteristics. This causes an erroneous detection of the alcohol concentration. However, the provision of the condenser "C1" eliminates this drawback.

Figure 14:
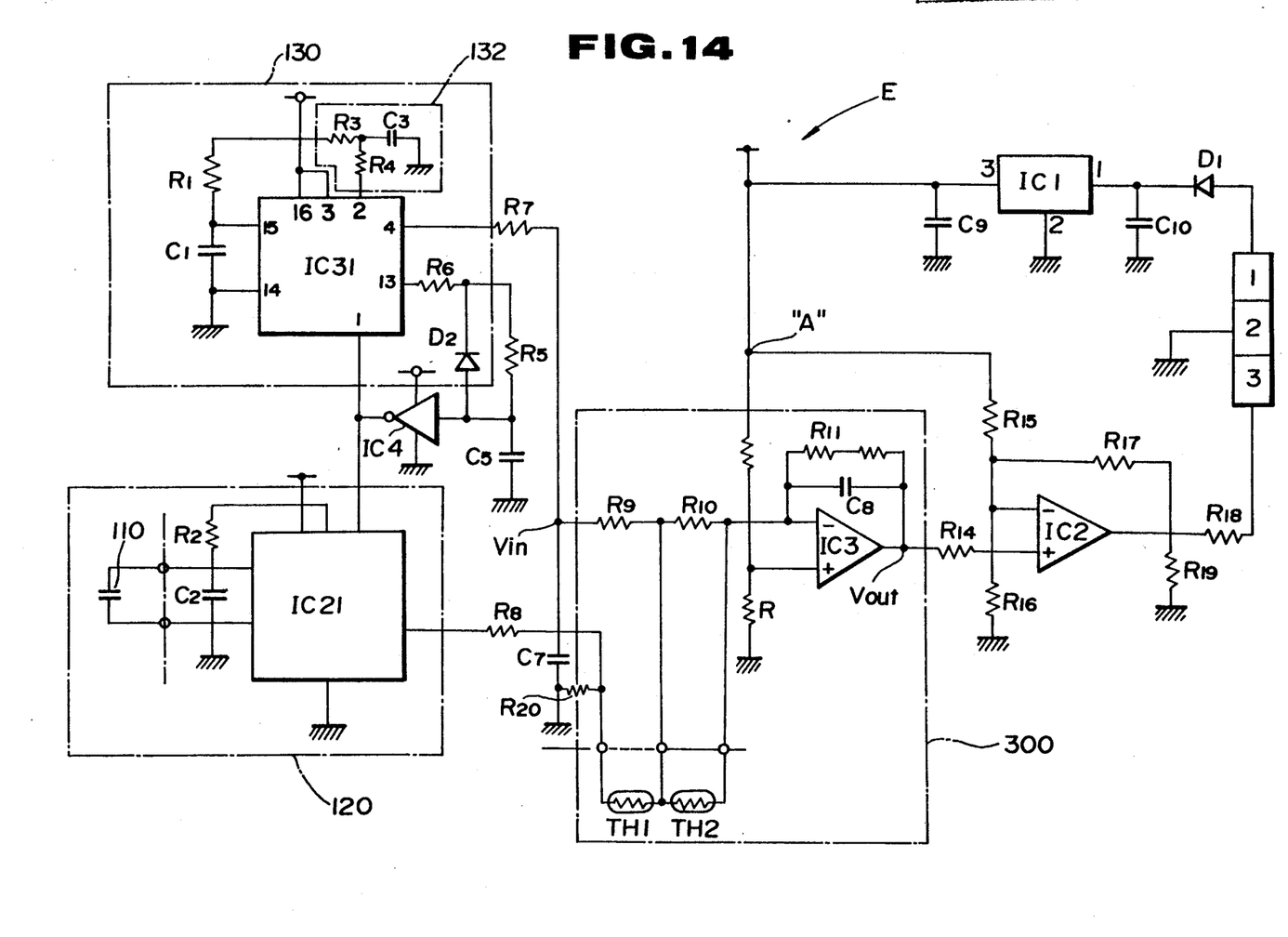
FIG. 14 is a circuit diagram of an alcohol concentration detecting device which is a fifth embodiment of the present invention.

Referring to FIG. 14, there is shown an alcohol concentration detecting device "E" of a fifth embodiment of the present invention.

In the fifth embodiment "E", there is employed a temperature compensating circuit 300 which performs temperature compensation for not only the capacitance detected by the alcohol sensor 110 but also for the functions of the first and second oscillating circuits 120 and 130. In fact, it has been determined that the capacitance "Cg" detected by the alcohol sensor 110 has a negative temperature characteristic of −0.503%/° C.

The temperature compensating circuit 300 comprises various resistors, a condenser, an integrated circuit "IC3", a first thermistor "TH1" and a second thermistor "TH2" which are connected in the illustrated manner. The first thermistor "TH1" is tightly received in a groove 12A (see FIG. 7) formed in the outer cylindrical electrode 12 and the second thermistor "TH2" is secured to the base board 80 (see FIG. 7). Thus, the first thermistor "TH1" detects the temperature of the mixed fuel, and the second thermistor "TH2" detects the temperature of the first and second oscillating circuits 120 and 130.

The values of temperatures detected by the thermistors "TH1" and "TH2" are converted into respective resistance values "$R_{TH1}$" and "$R_{TH2}$". Input and output voltage characteristics of the integrated circuit "IC3" are thus represented by the following equation:

$$V_{out} = -\frac{R11 + RX}{R7//R8//R20 + R9//R_{TH1} + R10//R_{TH2}} \cdot V_{in} + \left(1 + \frac{R11 + RX}{R7//R8//R20 + R9//R_{TH1} + R10//R_{TH2}}\right) \cdot \frac{R13}{R12 + R13} \cdot V_A \quad (6)$$

wherein:
$V_{IN}$: Input voltage of IC3,
$V_{OUT}$: Output voltage of IC3,
$V_A$: Voltage at point "A".

It is to be noted that the resistors "R9" and "R10" are used for linearizing the characteristics of the thermistors and adjusting the rate of their gains.

What is claimed is:

1. An alcohol concentration detecting device comprising:
    an alcohol sensor of a capacitance type having a probe portion which is to be submerged in an alcohol-mixed fuel, said alcohol sensor providing an output signal which varies in accordance with a concentration of alcohol in said alcohol-mixed fuel;
    a first oscillating circuit for receiving said output signal and said alcohol sensor and for outputting a variable pulse signal whose duty ratio is variable in accordance with said output signal;
    a second oscillating circuit for outputting a reference pulse signal, said reference pulse signal being the same as said pulse signal which is provided by said first oscillating circuit when there is no alcohol in said fuel; and
    an alcohol concentration detecting circuit which receives and compares said variable pulse signal and said reference pulse signal and outputs an alcohol concentration representing signal which is variable in accordance with a difference in duty ratio between said variable pulse signal and said reference pulse signal.

2. An alcohol concentration detecting device as claimed in claim 1, in which said first oscillating circuit comprises a fixed resistor, a condenser and an integrated circuit, said first oscillating circuit processing said output signal of said alcohol sensor at a frequency variable in accordance with a degree of capacitance sensed by said alcohol sensor.

3. An alcohol concentration detecting device as claimed in claim 2, in which said second oscillating circuit comprises a variable resistor, a fixed resistor, a condenser and an integrated circuit.

4. An alcohol concentration detecting device as claimed in claim 3, in which said alcohol concentration detecting circuit comprises a shaping and comparing circuit, a F/V conversion circuit and an amplifying circuit.

5. An alcohol concentration detecting device as claimed in claim 4, further comprising an indicating circuit which receives said alcohol concentration representing signal from said alcohol concentration detecting circuit to visually indicate said concentration of alcohol in said fuel.

6. An alcohol concentration detecting device as claimed in claim 1, in which said alcohol sensor comprises:
    an inner cylindrical electrode; and
    an outer cylindrical electrode which is coaxially and spacedly disposed about said inner cylindrical electrode, said outer cylindrical electrode having an axially extending slit through which a cylindrical space defined between said two cylindrical electrodes is in communication with the exterior of said alcohol sensor.

7. An alcohol concentration detecting device as claimed in claim 1, further comprising:
    a delay circuit coupled to said second oscillating circuit to delay the operation of said second oscillating circuit as compared with said first oscillating circuit.

8. An alcohol concentration detecting device as claimed in claim 7, further comprising:
    a timer circuit coupled between said alcohol concentration detecting circuit and an ignition switch of an engine, said timer circuit permitting operation of said alcohol concentration detecting circuit for a given time after said ignition switch is turned ON.

9. An alcohol concentration detecting device as claimed in claim 8, in which said first oscillating circuit comprises an integrated circuit and the capacity of said condenser in said first oscillating circuit is somewhat higher than the stray capacity of said integrated circuit in said first oscillating circuit.

10. An alcohol concentration detecting device as claimed in claim 7, further comprising:
    a temperature compensating circuit, coupled to said first and second oscillating circuits, for performing temperature compensation for said capacitance detected by said alcohol sensor and for said first and second oscillating circuits.

11. An alcohol concentration detecting device as claimed in claim 10, in which said temperature compensating circuit comprises:
    a first thermistor tightly mounted in said alcohol sensor at a position near said fuel to be measured; and
    a second thermistor attached to said alcohol sensor at a position where said first and second oscillating circuits are located.

12. An alcohol concentration detecting device comprising:
    an alcohol sensor of capacitance type having a probe portion which is to be submerged in an alcohol-mixed fuel, said alcohol sensor issuing an output signal which varies in accordance with the concentration of alcohol in the alcohol-mixed fuel;

an oscillating circuit which receives said output signal and issues a variable pulse signal which varies in accordance with said output signal;

a differentiating circuit which carries out a wave shaping of said variable pulse signal;

an integrating circuit which carries out another wave shaping of the pulse signal issued from said differentiating circuit;

an amplifying circuit which amplifies the wave-shaped pulse signal issued from said integrating circuit; and a signal reversing circuit treating the amplified wave-shaped pulse signal from said amplifying circuit thereby to produce a voltage signal, wherein said oscillating circuit is designed to issue a pulse signal which oscillates at a frequency ranging from about 1 MHz to 5 MHz.

* * * * *